(12) United States Patent  
Xu et al.

(10) Patent No.: US 9,051,273 B2
(45) Date of Patent: Jun. 9, 2015

(54) PHOSPHODIESTERASE 4 INHIBITOR CAPABLE OF AVOIDING VOMITING

(75) Inventors: Jiangping Xu, Ningbo (CN); Zhongzhen Zhou, Ningbo (CN)

(73) Assignee: Jiangping Xu, Ningbo, Zhejiang (CN)

( * ) Notice: Subject to any disclaimer, the term of this patent is extended or adjusted under 35 U.S.C. 154(b) by 0 days.

(21) Appl. No.: 14/373,347

(22) PCT Filed: Aug. 25, 2012

(86) PCT No.: PCT/CN2012/080593
§ 371 (c)(1),
(2), (4) Date: Jul. 18, 2014

(87) PCT Pub. No.: WO2013/123766
PCT Pub. Date: Aug. 29, 2013

(65) Prior Publication Data
US 2014/0364606 A1 Dec. 11, 2014

(30) Foreign Application Priority Data

Feb. 20, 2012 (CN) .......................... 2012 1 0037980

(51) Int. Cl.
*C07D 237/14* (2006.01)
*C07D 237/22* (2006.01)
*C07D 403/04* (2006.01)
*A61K 31/496* (2006.01)
*A61K 31/50* (2006.01)
*A61K 31/501* (2006.01)
*A61P 1/08* (2006.01)
*A61K 31/495* (2006.01)
*C07D 295/096* (2006.01)
*C07D 295/092* (2006.01)

(52) U.S. Cl.
CPC ............ *C07D 237/14* (2013.01); *A61K 31/495* (2013.01); *A61K 31/50* (2013.01); *C07D 295/096* (2013.01); *C07D 403/04* (2013.01); *A61K 31/496* (2013.01); *A61K 31/501* (2013.01); *C07D 237/22* (2013.01); *C07D 295/092* (2013.01)

(58) Field of Classification Search
CPC .. C07D 237/14; C07D 237/22; C07D 403/04; A61K 31/496; A61K 31/50; A61K 31/501; A61K 45/06
USPC ......... 544/238, 239; 514/247, 252.04, 252.02
See application file for complete search history.

(56) References Cited

U.S. PATENT DOCUMENTS

2014/0121166 A1* 5/2014 Kielian ........................ 514/17.7

* cited by examiner

*Primary Examiner* — Venkataraman Balasubramanian

(57) ABSTRACT

Phosphodiesterase 4 inhibitors without vomiting of the present invention are compounds or prodrugs or solvates represented by formula (I)

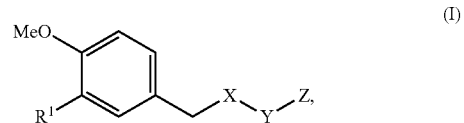

wherein $R^1$ is an independent methoxy, bromine and substituted aryl; X is an optionally substituted six-membered heterocyclic ring; Y is $-(CH_2)_n-$, $-NH(CH_2)_n-$, and $-NH(CH_2)_n-O-$, wherein n is any value among 0, 1, 2 and 3; Z is an optionally substituted aromatic ring or an optionally substituted heteroaromatic ring. Phosphodiesterase 4 inhibitor without vomiting of the present invention are novel biphenyl series PDE4D inhibitors, and can be applied to treat depression and Alzheimer's disease, improve cognitive ability and avoid vomiting.

1 Claim, No Drawings

PHOSPHODIESTERASE 4 INHIBITOR CAPABLE OF AVOIDING VOMITING

CROSS-REFERENCE TO RELATED APPLICATIONS

This PCT application is based on application No. 201210037980.3 filed in China on Feb. 20, 2012, the contents of which are incorporated hereinto by reference.

BACKGROUND OF THE PRESENT INVENTION

1. Field of Invention

The present invention relates to a technical field of compounds which are phosphodiesterase inhibitors, and more particularly to biphenyls PDE4D inhibitors without vomiting, which are adapted for treating depression and Alzheimer's disease, and improving cognitive ability.

2. Description of Related Arts

Phosphodiesterase 4 (PDE4) is mainly distributed in inflammatory cells (such as mast cells, macrophages, lymphocytes and epithelial cells) and neurons. PDE4 plays an important role in the central nervous system and immune system, and its specific inhibitors are regarded as new anti-inflammatory and central nervous system candidate drugs which act on the intracellular targets. PDE4 specifically catalyzes the hydrolysis of cAMP, and plays a key role in controlling the intracellular levels of cAMP. So PDE4 inhibition would lead to the accumulated concentration of intracellular cAMP, and then cause a variety of biological effects, such as anti-inflammation, anti-depression, enhancing memory, improving cognitive function and so on.

The first-generation PDE4 inhibitor such as rolipram has good antidepressant effect, but cannot be listed for its nausea and vomiting and other side effects from inhibiting PDE4. Compared with the first-generation PDE4 inhibitor, the second-generation PDE4 inhibitor has better therapeutic effect. However, the PDE4 inhibitor without vomiting has not yet been listed. Therefore, there is an urgent need to develop a new PDE4 inhibitor with reducing or even avoiding vomiting, and meanwhile with anti-depressing and improving the cognitive function.

PDE4 is encoded by four genes (A-D) that give rise to four isoforms. PDE4 isoforms (A-D) have multiple transcription units and promoters, and encoded over 20 different variants of this enzyme. By the researching results of Hanting zhang on PDE4D gene null mice, it is shown that PDE4D is closely related to depression and cognitive function, meanwhile related to vomiting. And many literatures confirmed this conjecture.

All experimental results show that PDE4 inhibitors may be competitive inhibitors of cAMP (Houslay, et al. 2005, DDT, 10, 1503-2119), which can also explain why the cure rate of the PDE4 inhibitors are low.

SUMMARY OF THE PRESENT INVENTION

The technology problem to be resolved in the present invention is to provide non-competitive phosphodiesterase 4 inhibitors without vomiting, and without competition with cAMP. This kind of compounds has higher inhibitory activity of PDE4 and PDE4D subtype. Comparable with the first-generation PDE4 inhibitor rolipram, animal experiments show that these inhibitors have better effects on improving learning and memory. Furthermore, the vomiting test of beagle dogs showed no obvious vomiting reaction. Therefore, these compounds are expected to be the first drugs without side effects such as vomiting, which are used in the treatment of depression and Alzheimer's disease, and improve cognitive deficits.

The technical solution adopted by the present invention to resolve the above technical problem is as follows.

Phosphodiesterase 4 inhibitors without vomiting are compounds or prodrugs or solvates represented by formula (I) of

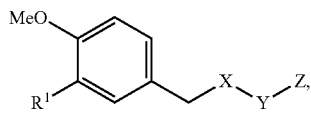

(I)

wherein, $R^1$ is independent methoxy, bromine and substituted aryl;

X is optionally substituted six-membered heterocycle;

Y is $-(CH_2)_n-$, $-NH(CH_2)_n-$, $-NH(CH_2)_n-O-$, wherein, the value of N can be one of 0, 1, 2 and 3;

Z is optionally substituted aromatic ring or optional substituted heteroaromatic ring.

Preferably, the R1 is

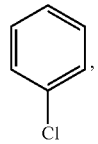

,

X—Y is

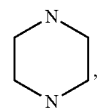

,

Z is optionally substituted aromatic ring.

Preferably, X is

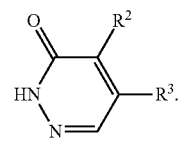

.

Compared with the prior art, the present invention relates to phosphodiesterase 4 inhibitors without vomiting are compounds or prodrugs or solvates represented by formula (I) of

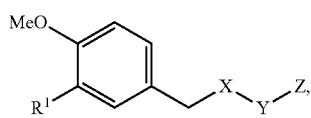

(I)

wherein, $R^1$ is independent methoxy, bromine and substituted aryl;

X is optionally substituted six-membered heterocycle;
Y is —(CH$_2$)$_n$—, —NH(CH$_2$)$_n$, —NH(CH$_2$)$_n$—O—,
wherein, the value of N can be one of 0, 1, 2 and 3;
Z is optionally substituted aromatic ring or optional substituted heteroaromatic ring.

The present invention relates to phosphodiesterase 4 inhibitors, non-competitive PDE4D inhibitors without vomiting and competition with cAMP. These inhibitors have higher inhibitory activity to PDE4 and PDE4D subtype. Comparable with the anti-depression drug, the first-generation PDE4 inhibitor rolipram, animal experiments show that these inhibitors have better effects on improving learning and memory. Furthermore, the vomiting test of beagle dogs showed no obvious vomiting reaction. Therefore, these compounds are expected to be the first drugs without side effects such as vomiting, which are used in the treatment of depression and Alzheimer's disease, and improve cognitive ability.

DETAILED DESCRIPTION OF THE PREFERRED EMBODIMENT

The present invention is further explained in detail with the accompanying drawings.

Phosphodiesterase 4 inhibitors without vomiting are compounds or prodrugs or solvates represented by formula (I) of (I)

wherein, R$^1$ is independent methoxy, bromine and substituted aryl;
X is optionally substituted six-membered heterocycle;
Y is —(CH$_2$)$_n$—, —NH(CH$_2$)$_n$, —NH(CH$_2$)$_n$—O—,
wherein, the value of N can be one of 0, 1, 2 and 3;
Z is optionally substituted aromatic ring or optional substituted heteroaromatic ring.

The above-mentioned phosphodiesterase 4 inhibitors are compounds or prodrugs or pharmaceutically acceptable salts or solvates represented by formula (II) of (II)

wherein Z is optionally substituted aromatic ring.

The above-mentioned phosphodiesterase 4 inhibitors are compounds or prodrugs or pharmaceutically acceptable salts or solvates represented by formula (III) of (III)

wherein, R$^1$ is independent methoxy and substituted aryl;
Y is —(CH$_2$)$_n$—, —NH(CH$_2$)$_n$, —NH(CH$_2$)$_n$—O—,
wherein, the value of N can be one of 0, 1, 2 and 3;
Z is optionally substituted aromatic ring or optional substituted heteroaromatic ring.

The formula (II) series compounds are shown as follows:

(II)

| Compd. | Z |
|---|---|
| II-1 | 2-methoxyphenyl |
| II-2 | 2-chlorophenyl |

The formula (III) series compounds are shown as follows:

(III)

| Compd. | R$^1$ | R$^2$ | R$^3$ | Y | Z |
|---|---|---|---|---|---|
| III-1 | 3-chlorophenyl | Cl | Cl | H | \ |
| III-2 | 3-chlorophenyl | H | H | —N(CH$_2$CH$_2$)$_2$N— | 2-chlorophenyl |
| III-3 | 3-chlorophenyl | H | H | —NHCH$_2$CH$_2$O— | 2-methoxyphenyl |
| III-4 | Br | | H | H | —NH CH$_2$CH$_2$O— | 2-methoxyphenyl |
| III-5 | MeO | | H | H | —NH CH$_2$CH$_2$O— | 2-methoxyphenyl |

The compound of the present invention represented by formula (I) and formula (II) can be synthesized by the well-known method described in the chemical literatures. The method adapted for the present invention is summarized in Scheme 1.

Scheme 1

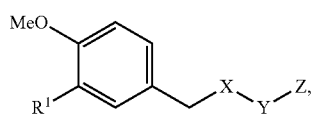
NBS / CCl$_4$

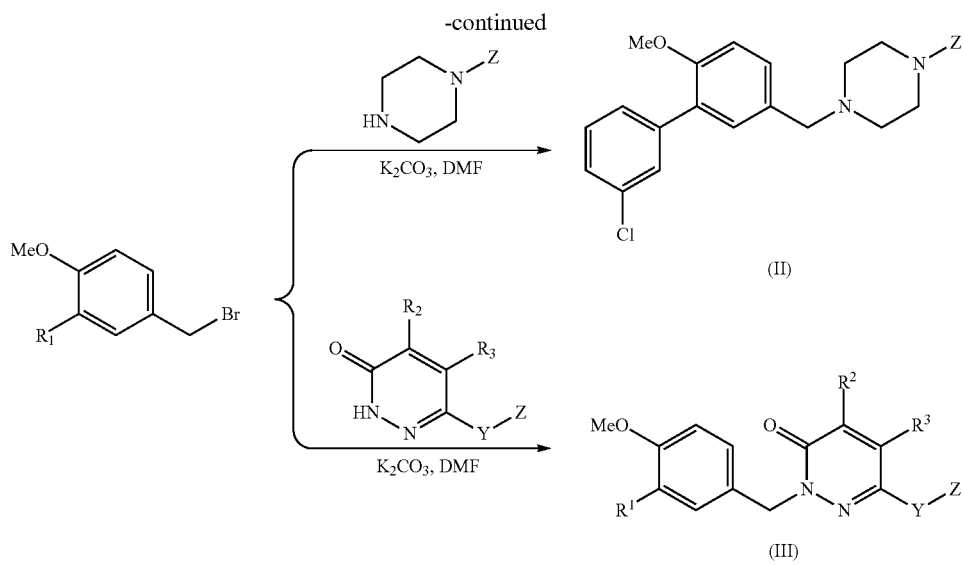

3-substituted-4-methoxy toluene (2 mmol) was added into 50 ml two-necked round bottom flask, and then 0.356 g (2 mmol) N-bromosuccinimide (NBS) and 20 ml anhydrous carbon tetrachloride were added. Then the reaction mixture was heated until refluxing, and monitored by thin layer chromatography. After completing the reaction, the reaction mixture was filtered. The filtrate was concentrated under reduced pressure, and the obtained residue was the crude product, 3-substituted-4-methoxy bromide methyl benzene, then directly goes into the next reaction without isolation.

2 mmol heterocyclic amine was added into 25 ml two-necked round bottom flask, and then 10 ml anhydrous DMF and 0.417 g anhydrous potassium carbonate (3 mmol) was added. The mixture was stirred for 1 h at room temperature, and then the crude methyl bromide 3-substituted-4-methoxy bromide methyl benzene obtained in the above step was added. Then the reaction mixture was stirred for 12 h at room temperature, monitored by thin layer chromatography. After completing the reaction, the reaction mixture was filtered. The filtrate was concentrated under reduced pressure, and the crude product is obtained. The target compound is obtained by column chromatography isolation.

The spectral data of the target compound is:

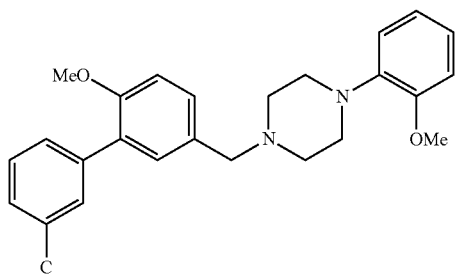 [SMILES: COc1ccc(CN2CCN(c3ccccc3OC)CC2)cc1-c1cccc(C)c1]

Compound II-1 (ZX-I01): Yield: 65%; ESI-MS: m/z 424.0 ([M+H]$^+$), 446.0 ([M+Na]$^+$); $^1$H NMR (400 MHz, CDCl$_3$): 2.65~2.70 (m, 4H), 3.05~3.15 (m, 4H), 3.81 (s, 3H, MeO), 3.85 (s, 3H, MeO), 3.89 (s, 2H, CH2), 6.84~7.01 (m, 5H), 7.27~7.36 (m, 4H), 7.41 (s, 1H), 7.53 (s, 1H);

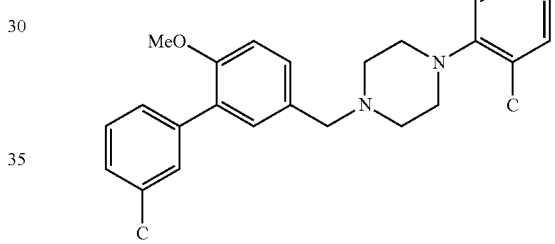

Compound II-2 (ZX-I02): Yield: 63%; ESI-MS: m/z 427.5 (M$^+$), 428.5 ([M+1]$^+$), 429.5 ([M+2]$^+$); $^1$H NMR (400 MHz, CDCl$_3$): 2.63~2.70 (m, 4H), 3.09~3.12 (m, 4H), 3.82 (s, 3H, MeO), 3.89 (s, 2H, CH$_2$), 6.94~6.98 (m, 2H), 7.03 (d, J=8.0 Hz, 1H), 7.21 (t, J=7.6 Hz, 1H), 7.28~7.40 (m, 5H), 7.43 (s, 1H), 7.55 (s, 1H);

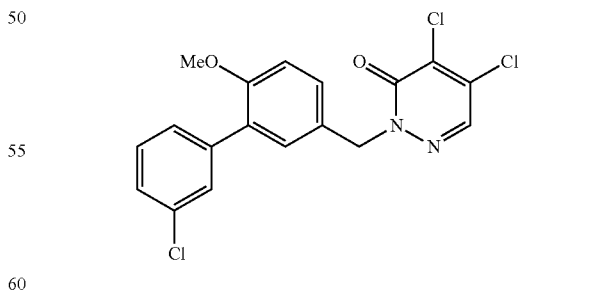

Compound III-1 (ZX-I03): Yield: 43%; ESI-MS: m/z 395.6 (M), 396.5 ([M+1]$^+$), 397.5 ([M+2]$^+$); $^1$H NMR (400 MHz, CDCl3): 3.80 (s, 3H, MeO), 5.29 (s, 2H, CH$_2$), 6.92 (d, J=7.6 Hz, 1H), 7.29~7.39 (m, 3H), 7.45~7.48 (m, 2H), 7.64 (d, J=2.0 Hz, 1H), 7.77~7.8 (m, 2H);

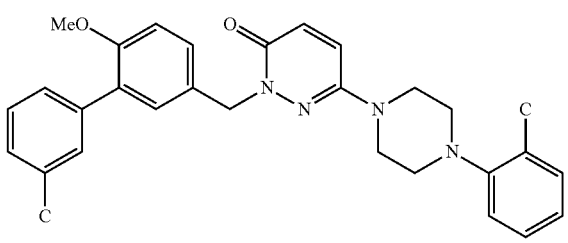 [SMILES: COc1ccc(Cn2nc(N3CCN(c4ccccc4C)CC3)ccc2=O)cc1-c1cccc(C)c1]

Compound III-2 (ZX-I06): Yield: 33%; ESI-MS: m/z 521.5 (M$^+$), 522.5 ([M+1]$^+$), 523.5 ([M+2]$^+$); $^1$H NMR (400 MHz, CDCl$_3$): 3.20~3.30 (m, 4H), 3.50~3.60 (m, 4H), 3.82 (s, 3H, MeO), 5.14 (s, 2H, CH$_2$), 6.86~7.00 (m, 2H), 7.08 (t, J=8.0 Hz, 1H), 7.15 (d, J=9.6 Hz, 1H), 7.28~7.34 (m, 4H), 7.39~7.44 (m, 3H), 7.46 (d, J=8.4 Hz, 1H), 7.51 (s, 1H), 7.68 (d, J=1.6 Hz, 1H);

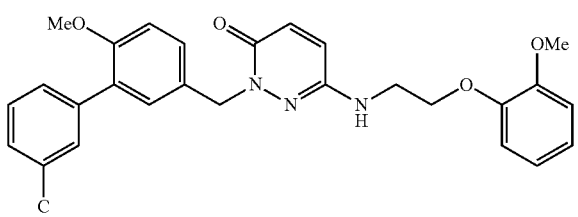 [SMILES: COc1ccccc1OCCNc1ccc(=O)n(Cc2ccc(OC)c(-c3cccc(C)c3)c2)n1]

Compound III-3 (ZX-I07): Yield: 45%; ESI-MS: m/z 492.6 (M), 493.6 ([M+1]$^+$), 494.6 ([M+2]$^+$), 514.6 ([M+Na]$^+$), 530.6 ([M+K]$^+$); $^1$H NMR (400 MHz, CDCl$_3$): 3.64 (t, J=4.8 Hz, 2H), 3.79 (s, 3H, MeO), 3.84 (s, 3H, MeO), 4.13 ((t, J=4.8 Hz, 2H), 5.16 (s, 2H, CH$_2$), 6.78 (d, J=9.6 Hz, 1H), 6.85~6.98 (m, 6H), 7.28~7.44 (m, 4H), 7.505 (s, 1H), 8.02 (s, 1H);

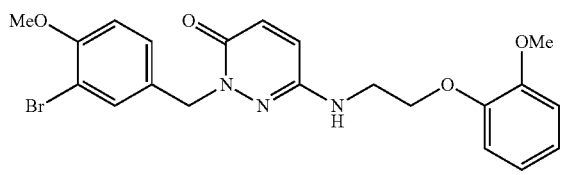 [SMILES: COc1ccc(Cn2nc(NCCOc3ccccc3OC)ccc2=O)cc1Br]

Compound III-4 (ZX-I11): Yield: 42%; ESI-MS: m/z 482.4 ([(M−1)+Na]$^+$), 484.4 ([(M+1)+Na]$^+$); $^1$H NMR (400 MHz, CDCl$_3$): 3.64 (t, J=4.8 Hz, 2H), 3.85 (s, 3H, MeO), 3.96 (s, 3H, MeO), 4.18 ((t, J=4.8 Hz, 2H), 5.08 (s, 2H, CH$_2$), 6.73~6.99 (m, 5H), 7.36 (d, J=7.2 Hz, 1H), 7.53~7.55 (m, 1H), 7.65 (d, J=1.2 Hz, 1H), 7.72~7.74 (m, 1H);

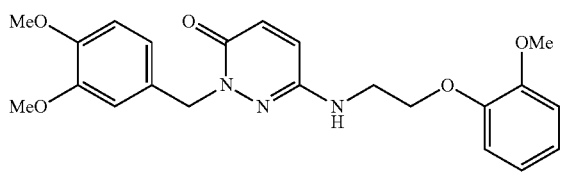 [SMILES: COc1ccc(Cn2nc(NCCOc3ccccc3OC)ccc2=O)cc1OC]

Compound III-5 (ZX-I12): Yield: 28%; ESI-MS: m/z 412.7 ([M+1]$^+$), 434.7 ([M+Na]$^+$), 450.7 ([M+K]$^+$); $^1$H NMR (400 MHz, CDCl3): 3.79 (s, 3H, MeO), 3.81 (s, 3H, MeO), 3.85~3.87 (m, 5H, MeO, CH$_2$), 4.19 (t, J=5.2 Hz, 2H), 4.68 (s, 2H, CH$_2$), 6.76~6.94 (m, 7H), 7.00 (d, J=10 Hz, 1H), 7.34 (d, J=10 Hz, 1H);

Phosphodiesterase 4 inhibitory activity test
1. Experimental Method
2. Phosphodiesterase 4 inhibitory activity test utilizes IMAP technology, which is called immobilized metal ion affinity-based fluorescence polarization and provide a stable and accurate approach for determining the inhibitory potential of compounds.
3. Experimental Results

TABLE 1

The inhibitory activities of new PDE4 inhibitors II-1, II-2, III-1~III-3 to PDE4CAT, PDE4D4 and PDE4D5

| Compound | PDE4CAT IC$_{50}$ | PDE4D4 IC$_{50}$ | PDE4D5 IC$_{50}$ |
|---|---|---|---|
| II-1 (ZX-I01) | 28.4 μM | 115 μM | 83.7 μM |
| II-2 (ZX-I02) | 18.1 μM | 141 μM | 50.9 μM |
| III-1 (ZX-I03) | 25.6 μM | 22.4 μM | 8.32 μM |
| III-2 (ZX-I06) | 16.7 μM | 137 μM | 110 μM |
| III-3 (ZX-I07) | 3.87 μM | 7.82 μM | 8.48 μM |
| Rolipram | 4.92 μM | 0.48 μM | 0.24 μM |

TABLE 2

The inhibitory activities of new PDE4 inhibitors ZX-I11 and ZX-I12

| Compound | PDE4CAT IC$_{50}$ |
|---|---|
| III-4 (ZX-I11) | 44.0 μM |
| III-5 (ZX-I12) | 66.9 μM |
| Rolipram | 5.36 μM |

Animal Experiments
1. The effects of the new PDE4 inhibitor III-3 on the learning and memory with scopolamine-induced cognitive deficits in mice
1.1 Method
60 kunming mice are randomly divided into 6 groups, namely blank control group, scopolamine group, rolipram control group, and III-3 low, middle and high dose groups, each group includes 10 mice. After being continuously administered with veh or compounds for 1 week, the behavioral tests are determined by Morris water maze. 20 minutes before test, saline is given into the blank control mice through intraperitoneal injection, while scopolamine is intraperitoneally injected to the other five groups. These mice are continuously trained for 4 days, and the space exploration experiment is performed on the fifth day for recording the latency to target quadrant, the number of crossing and retention time in the target quadrant during the test period of each mice.

TABLE 3

The effects of the new PDE4 inhibitor III-3 on the learning and memory behavioral performance in the Morris water maze ($\bar{X} \pm S$)

| Group | Latency to target quadrant (t/s) | The number of crossing target quadrant | Retention time in target quadrant time (t/s) |
|---|---|---|---|
| control | 10.81 ± 2.62* | 6.75 ± 0.65** | 45.88 ± 3.18* |
| scopolamine | 37.21 ± 7.76 | 3.33 ± 0.55 | 32.00 ± 3.16 |
| scopo. + Rolipram 0.5 mg/kg | 16.09 ± 3.29 | 6.89 ± 0.59** | 38.34 ± 3.65 |
| scopo. + III-3 0.2 mg/kg | 9.96 ± 2.32* | 6.67 ± 1.29 | 42.78 ± 4.56* |

TABLE 3-continued

The effects of the new PDE4 inhibitor III-3 on the
learning and memory behavioral performance in the
Morris water maze ($\overline{X} \pm S$)

| Group | Latency to target quadrant (t/s) | The number of crossing target quadrant | Retention time in target quadrant time (t/s) |
|---|---|---|---|
| F | 7.599 | 4.296 | 2.601 |
| P | 0.001 | 0.012 | 0.070 |

Note:
*$P < 0.05$,
**$P < 0.01$ compared with the scopolamine-treated group, scopo. is the abbreviation of scopolamine.

2. Preliminary assessing the potential vomiting effects of new PDE4 inhibitor III-3

2.1 Method

Six beagle dogs were randomly divided into two groups, vehicle (5% DMSO, 1 ml/kg) or rolipram with the dose 0.5 mg/kg (dissolved in 5% DMSO with the final concentration is 0.5 mg/ml) were administered by oral gavage at the volume of 1 mL/kg. The potential vomiting observation time is 120 minutes after the oral administration. The latency was determined by the interval time from the oral administration of the drugs to the nausea, retching, a lot of salivation and vomiting of gastric contents. The incidence of emesis was also recorded. After one week, six beagle dogs are renewedly randomly divided into two groups, 0.5 mg/kg rolipram and the III-3 1.0 mg/kg were oral administered with the volume 1 ml/kg. and continuously observe for 120 minutes by the same method.

1.2 Experimental Results

TABLE 4

The emesis induced by the new PDE4 inhibitor III-3 in beagle dogs

| Treatment | Latency period (min) | Incidence of emesis |
|---|---|---|
| Vehicle | >120 | 0/3 |
| Rolipram(0.5 mg/kg) | 10.67 ± 2.68 | 6/6 |
| III-3(1.0 mg/kg) | >120 | 0/3 |

The best embodiment of the present invention has illustrated that all modifications and variations made by the ordinary technology person skilled in the art are encompassed within the scope of the present invention.

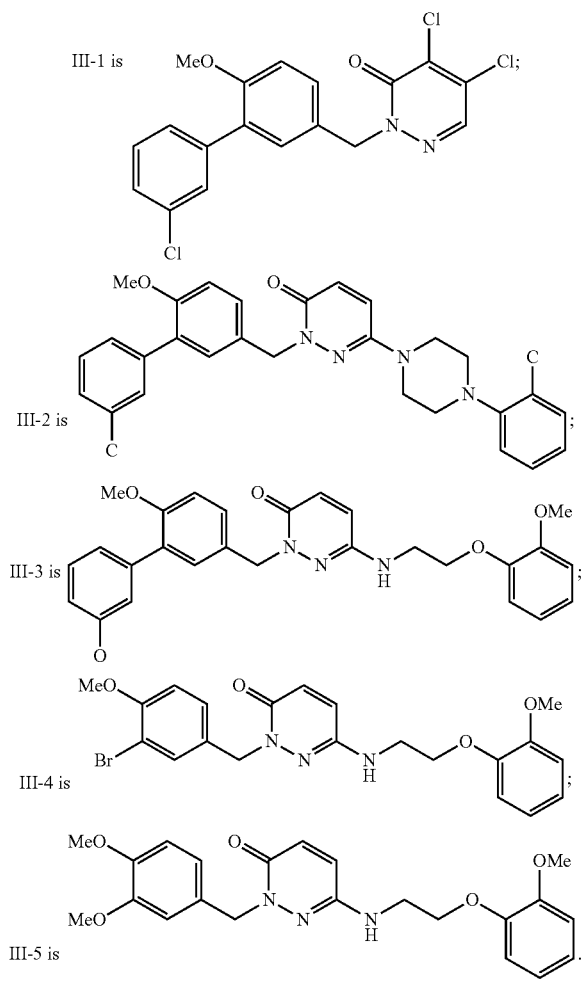

What is claimed is:

1. A Phosphodiesterase 4 inhibitor capable of avoiding vomiting, wherein a structural formula of the inhibitor is III-1, III-2, III-3, III-4 or 1115, wherein: